US012239574B2

(12) United States Patent
Peterson

(10) Patent No.: US 12,239,574 B2
(45) Date of Patent: Mar. 4, 2025

(54) ASPIRATING CUTTER AND METHOD OF USE

(71) Applicant: Medical Instrument Development Laboratories, Inc., San Leandro, CA (US)

(72) Inventor: Erik William Peterson, Walnut Creek, CA (US)

(73) Assignee: Medical Instrument Development Laboratories, Inc., San Leandro, CA (US)

(*) Notice: Subject to any disclaimer, the term of this patent is extended or adjusted under 35 U.S.C. 154(b) by 411 days.

(21) Appl. No.: 17/592,663

(22) Filed: Feb. 4, 2022

(65) Prior Publication Data

US 2022/0151831 A1 May 19, 2022

Related U.S. Application Data

(62) Division of application No. 16/076,394, filed as application No. PCT/US2015/021730 on Mar. 20, 2015, now Pat. No. 11,241,333.

(Continued)

(51) Int. Cl.
*A61F 9/007* (2006.01)
*A61F 9/008* (2006.01)

(52) U.S. Cl.
CPC ...... *A61F 9/00709* (2013.01); *A61F 9/00763* (2013.01); *A61F 9/00825* (2013.01);
(Continued)

(58) Field of Classification Search
CPC .. A61F 9/007; A61F 9/00709; A61F 9/00736; A61F 9/00763; A61F 9/00781; A61F 2009/00874; A61B 17/32002; A61B 2017/320024; A61B 17/320783; A61B 2017/320791

See application file for complete search history.

(56) References Cited

U.S. PATENT DOCUMENTS 3,815,604 A   6/1974 O'Malley et al.
4,099,529 A   7/1978 Peyman
(Continued)

FOREIGN PATENT DOCUMENTS

EP    2168540 B1    3/2010
WO    2014039836 A1    3/2014

OTHER PUBLICATIONS

International Search Report and Written Opinion for Application No. PCT/US2015/021730 dated Aug. 19, 2015 (20 pages).

*Primary Examiner* — Diane D Yabut
*Assistant Examiner* — Christian D Knauss
(74) *Attorney, Agent, or Firm* — Michael Best & Friedrich LLP

(57) ABSTRACT

An ophthalmic surgical cutting apparatus for cutting biological material including a handle, an outer tube attached to the handle and having a closed tip, a port formed in a side wall of the outer tube with a cusp formed by two or more intersecting surfaces, and an inner tube slidable within the outer tube and having a longitudinal axis and an open tip. The inner tube is in fluid communication with the handle, and the cusp of the port and the open tip interface during a cutting motion to fracture and cut biological materials and direct cut materials radially inward into the port.

11 Claims, 9 Drawing Sheets

Related U.S. Application Data

(60) Provisional application No. 62/028,432, filed on Jul. 24, 2014, provisional application No. 61/968,109, filed on Mar. 20, 2014.

(52) U.S. Cl.
CPC . *A61B 2217/005* (2013.01); *A61F 2009/0087* (2013.01); *A61F 2009/00874* (2013.01); *A61F 2009/00887* (2013.01)

(56) References Cited

U.S. PATENT DOCUMENTS

| | | | |
|---|---|---|---|
| 4,111,207 A | 9/1978 | Seiler, Jr. | |
| 4,246,902 A | 1/1981 | Martinez | |
| 4,282,884 A * | 8/1981 | Boebel | A61B 10/04 600/564 |
| 4,530,356 A | 7/1985 | Helfgott et al. | |
| 4,662,869 A | 5/1987 | Wright | |
| 5,106,364 A * | 4/1992 | Hayafuji | A61F 9/00763 606/171 |
| 5,217,479 A | 6/1993 | Shuler | |
| 5,346,497 A | 9/1994 | Simon et al. | |
| 5,472,440 A | 12/1995 | Beckman | |
| 5,487,725 A | 1/1996 | Peyman | |
| 5,540,708 A | 7/1996 | Lim et al. | |
| 5,601,583 A | 2/1997 | Donahue et al. | |
| 5,693,063 A | 12/1997 | Van Wyk et al. | |
| 6,027,493 A | 2/2000 | Donitzky et al. | |
| 6,027,514 A | 2/2000 | Stine et al. | |
| 6,120,498 A | 9/2000 | Jani et al. | |
| 6,156,049 A | 12/2000 | Lovato et al. | |
| 6,322,557 B1 | 11/2001 | Nikolaevich et al. | |
| 6,342,061 B1 | 1/2002 | Kauker et al. | |
| 6,428,501 B1 | 8/2002 | Reynard | |
| 6,533,749 B1 | 3/2003 | Mitusina et al. | |
| 6,949,096 B2 | 9/2005 | Davison et al. | |
| 7,182,759 B2 | 2/2007 | Kadziauskas et al. | |
| 8,080,029 B2 | 12/2011 | Charles | |
| 8,475,482 B2 | 7/2013 | Palmer et al. | |
| 8,690,940 B2 | 4/2014 | Kleinman | |
| 2004/0167504 A1 | 8/2004 | Thyzel | |
| 2005/0234441 A1 | 10/2005 | Bisch et al. | |
| 2006/0271082 A1 | 11/2006 | Kirchhevel et al. | |
| 2011/0144638 A1 | 6/2011 | Heeren et al. | |
| 2011/0144641 A1 | 6/2011 | Dimalanta, Jr. et al. | |
| 2011/0201881 A1 | 8/2011 | Emch | |
| 2012/0041461 A1 | 2/2012 | McCollam | |
| 2012/0259320 A1 | 10/2012 | Loesel et al. | |
| 2013/0231605 A1 | 9/2013 | Walter | |
| 2014/0052113 A1 | 2/2014 | Kuehnert et al. | |
| 2014/0364885 A1 * | 12/2014 | Wells | A61F 9/00763 606/170 |
| 2015/0182379 A1 | 7/2015 | Fantoni et al. | |
| 2016/0022489 A1 | 1/2016 | Hartstra | |

\* cited by examiner

ASPIRATING CUTTER AND METHOD OF USE

CROSS-REFERENCE TO RELATED APPLICATIONS

This application is a divisional of U.S. application Ser. No. 16/076,394, filed Aug. 8, 2018, which is a 371 of PCT/US2015/021730, filed Mar. 20, 2015, and claims priority U.S. Provisional Patent Application No. 61/968,109, filed Mar. 20, 2014, and U.S. Provisional Patent Application No. 62/028,432, filed Jul. 24, 2014, the entire contents of each of which are hereby incorporated by reference.

BACKGROUND

The present invention relates to surgical hand tools for ophthalmic surgeries. More particularly, embodiments of the invention relate to aspirating cutters.

Aspirating cutters are commonly used in ophthalmic surgery, notably for cutting and removing vitreous humor that fills the space between the lens and retina of the eyeball, as illustrated in FIG. 1. Vitreous humor is a soft but tough material and is easily deformed into a port of an aspirating cutter under the influence of a vacuum. Various pathological membranes inside of the eye can also be cut with an aspirating cutter, for example, a mildly cataractous lens is. A fully-developed cataract, however, is too hard to be deformed into the port and, consequently, a different type of instrument is commonly used for cataract removal.

The instrument commonly used for cataract removal (i.e., a phacoemulsification instrument) has an open-ended needle vibrating at ultrasonic frequencies. The vibration breaks up lens material touching the edge of the needle, allowing the fragments to be aspirated out through the needle body. This instrument presents several problems, however. It is considerably expensive as a single-use instrument, and if used as a multi-use instrument there is a potential for infection resulting from inadequate re-sterilization. Further, the ultrasonic energy delivered into the eye for the removal procedure has the potential to damage the cornea.

SUMMARY

There is a need, therefore, for a cost-effective device which breaks up and removes the lens in a safer fashion. An aspirating cutter having certain features directed toward cutting harder materials can fulfill this need. Additionally, such an aspirating cutter may be used with other instruments for fragmenting harder materials.

In one aspect, the invention provides an ophthalmic surgical cutting apparatus, for example an ophthalmic surgical apparatus, for cutting biological material. The apparatus include a handle, an outer tube attached to the handle and having a closed tip, and a port formed in a side wall of the outer tube. The port including a cusp formed by two or more intersecting surfaces. The apparatus also includes an inner tube slidable within the outer tube and having a longitudinal axis and an open tip. The inner tube is also in fluid communication with the handle. The cusp of the port and the open tip interface during a cutting motion to fracture and cut biological materials and direct cut materials radially inward into the port.

In another aspect, the invention provides an ophthalmic surgical cutting apparatus for cutting biological material including a handle, an outer tube attached to the handle and having a closed tip, a port formed in a side wall of the outer tube with an edge, and an inner tube slidable within the outer tube and having a longitudinal axis and an open tip with a cusp. The cusp is formed by two or more intersecting surfaces, and the inner tube is in fluid communication with the handle. The edge of the port and the cusp of the open tip interface during a cutting motion in which the inner tube is moved toward the closed tip.

In another aspect, the invention provides an ophthalmic surgical cutting apparatus for cutting biological material including a handle, an outer tube attached to the handle and having an open tip, and an inner tube slidable within the outer tube and having a closed tip. The inner tube is also in fluid communication with the handle. The apparatus also includes a port formed in a side wall of the inner tube and including an edge. The edge of the port and the open tip interface to fracture and cut biological materials, and the inner tube is extendable beyond the outer tube.

In another aspect, the invention provides an ophthalmic surgical cutting apparatus for cutting biological material including a handle, an outer tube attached to the handle and having a closed tip, a first port formed in a side wall of the outer tube with a cusp formed by two or more intersecting surfaces, and an inner tube slidable within the outer tube and having a longitudinal axis and an open tip. The inner tube is also in fluid communication with the handle. The apparatus also includes a second port formed in a side wall of the inner tube. The cusp of the first port and the open tip of the inner tube interface during a cutting motion to fracture and cut biological materials and direct cut materials radially inward into the first port.

In another aspect, the invention provides a method of operating an ophthalmic surgical cutting apparatus including a handle, an outer tube with a closed tip, an inner tube with an open tip, a first port formed in a side wall of the outer tube, and a second port formed in a side wall of the inner tube. The method includes operating the ophthalmic surgical cutting apparatus in a first mode of operation including positioning the inner tube in an extended position, and aspirating biological tissue through the first and second ports. The method also includes operating the ophthalmic surgical cutting apparatus in a second mode of operation including positioning the inner tube in the extended position, aspirating biological tissue through the first and second ports, actuating the inner tube to move from the extended position to a retracted position when the biological material is occluding the second port, and returning the inner tube to the extended position. The method also includes operating the ophthalmic surgical cutting apparatus in a third mode of operation including positioning the inner tube in the retracted position, aspirating biological tissue through the first port, actuating the inner tube to move from the retracted position to the extended position when biological material is occluding the first port, and returning the inner tube to the retracted position.

Other aspects will become apparent by consideration of the detailed description and accompanying drawings.

DETAILED DESCRIPTION

Before any embodiments are explained in detail, it is to be understood that the apparatus is not limited in its application to the details of construction and the arrangement of components set forth in the following description or illustrated in the following drawings. The disclosure is capable of supporting other embodiments and of being practiced or of being carried out in various ways.

Figure 1:
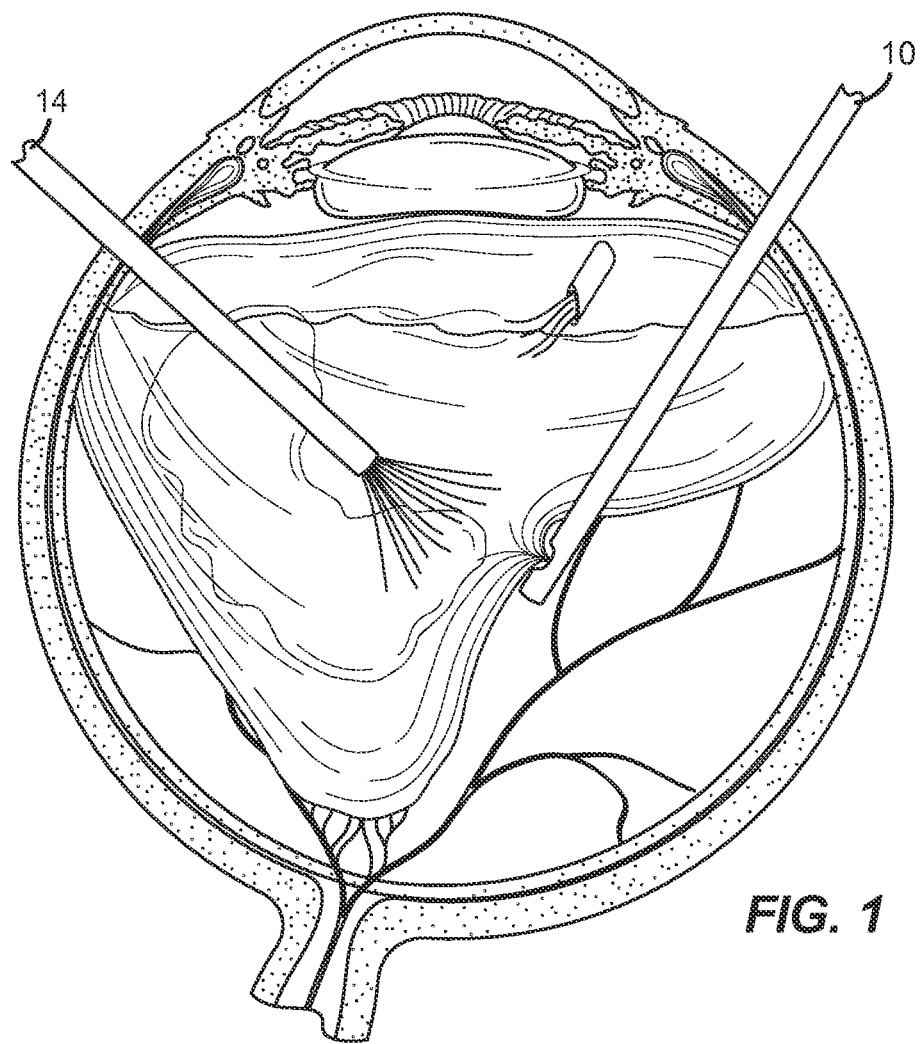
FIG. 1 is a cross-sectional view of an eye into which an aspirating cutter and a light source have been inserted.
Figure 2:
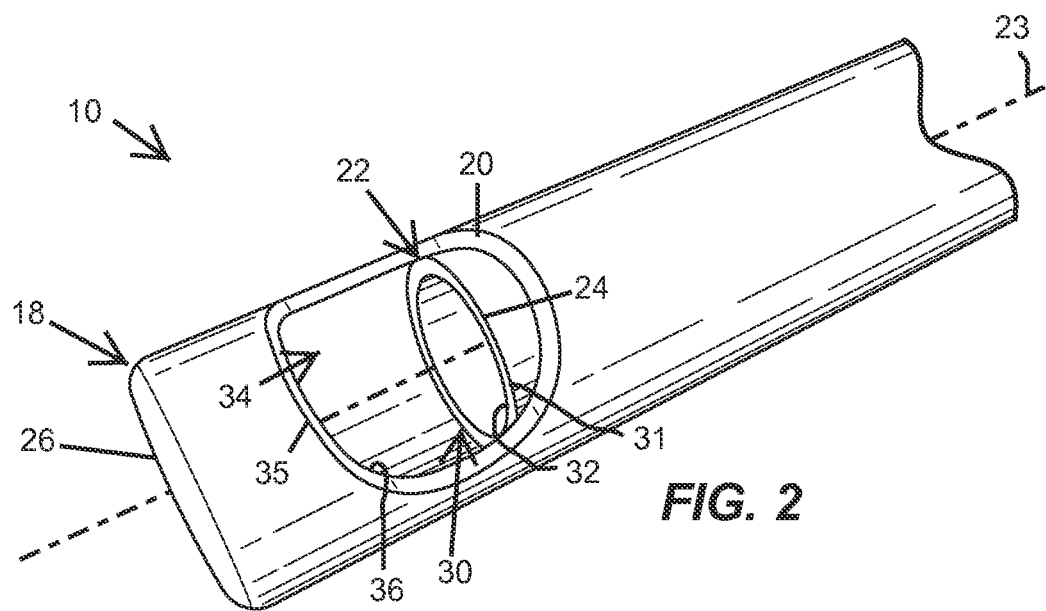
FIG. 2 is a perspective view of a portion of an aspirating cutter.
Figure 3:
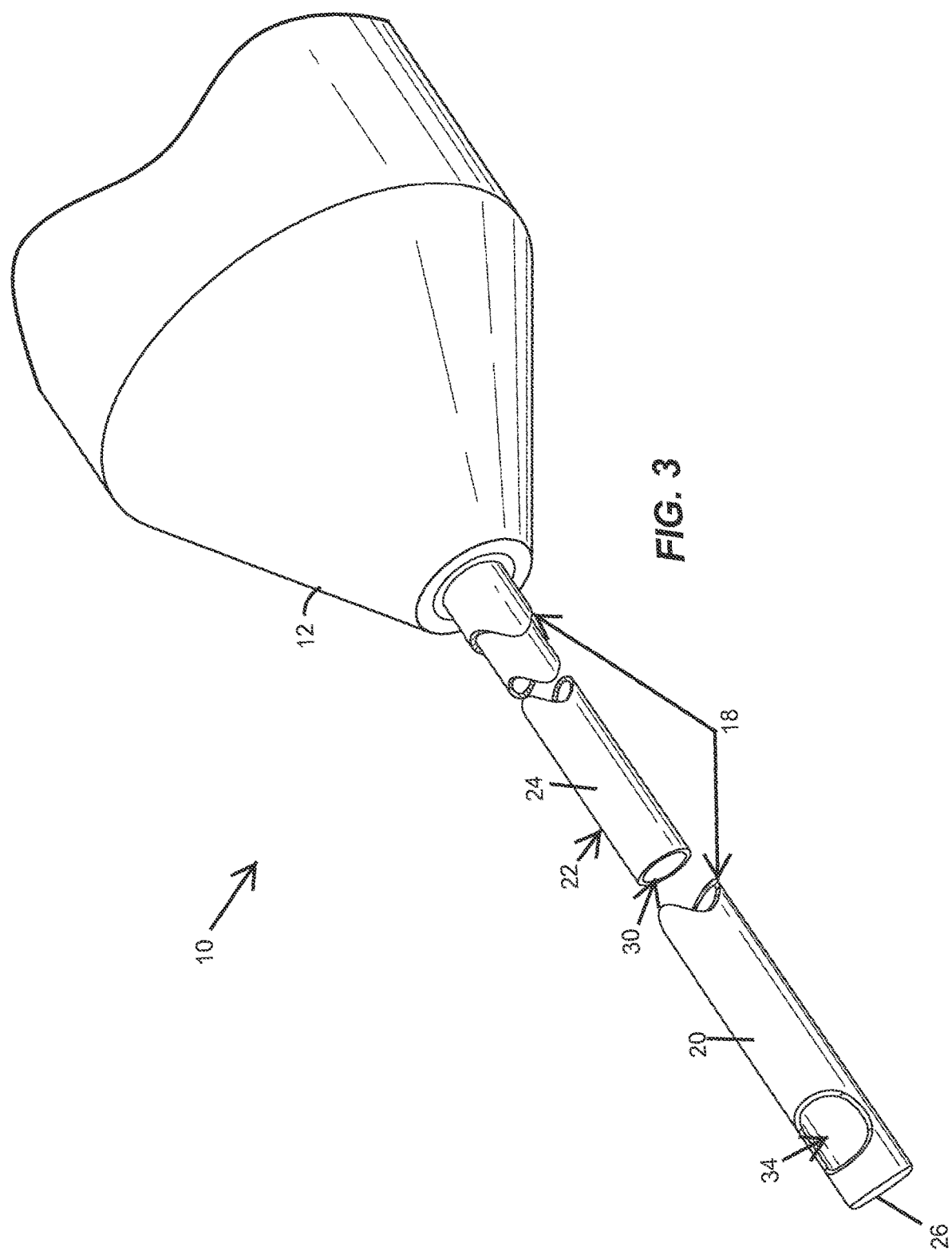
FIG. 3 is a perspective view of a portion of the aspirating cutter partially shown in FIG. 2 illustrating the inner and outer tubes in an exploded view.

FIG. 1 illustrates an eye into which an aspirating cutter 10 and a light source 14 have been inserted, corresponding to a manner in which devices would be inserted during a vitrectomy surgery, or the like. As illustrated in FIGS. 2 and 3, the aspirating cutter 10 includes an outer tube 18 and a coaxial inner tube 22 movable relative to each other along a common longitudinal axis 23. The tubes 18, 22 are attached to a handle 12, which is graspable by a user to manipulate the aspirating cutter 10. The outer tube 18 and the inner tube 22 include respective annular side walls 20, 24, constructed, for example, from surgical stainless steel.

The outer tube 18 is formed with a closed tip 26 at an end furthest away from the handle 12, and includes an opening or port 34 formed into the annular side wall 20 near the closed tip 26 for aspirating and/or cutting. The portion of the annular side wall 20 defining the rim of the port 34 includes an outer edge 35 and an inner edge 36.

The inner tube 22 is formed with an open tip 30 at an end furthest away from the handle 12, which end also defines a rim having an outer edge 31 and an inner edge 32. As shown in FIGS. 2 and 3, the outer tube 18 has an inside diameter greater than the outside diameter of the inner tube 22 such that the inner tube 22 is received inside the outer tube 18 and is slidable within it.

Figure 4:
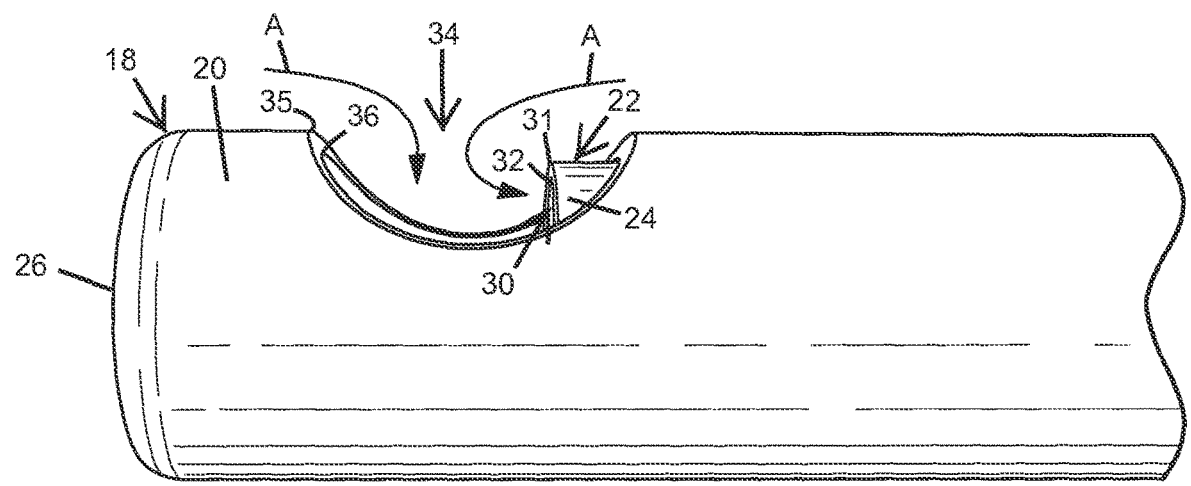
FIG. 4 is a side view of the aspirating cutter partially shown in FIG. 2 illustrating the direction of airflow during aspiration.
Figure 5:
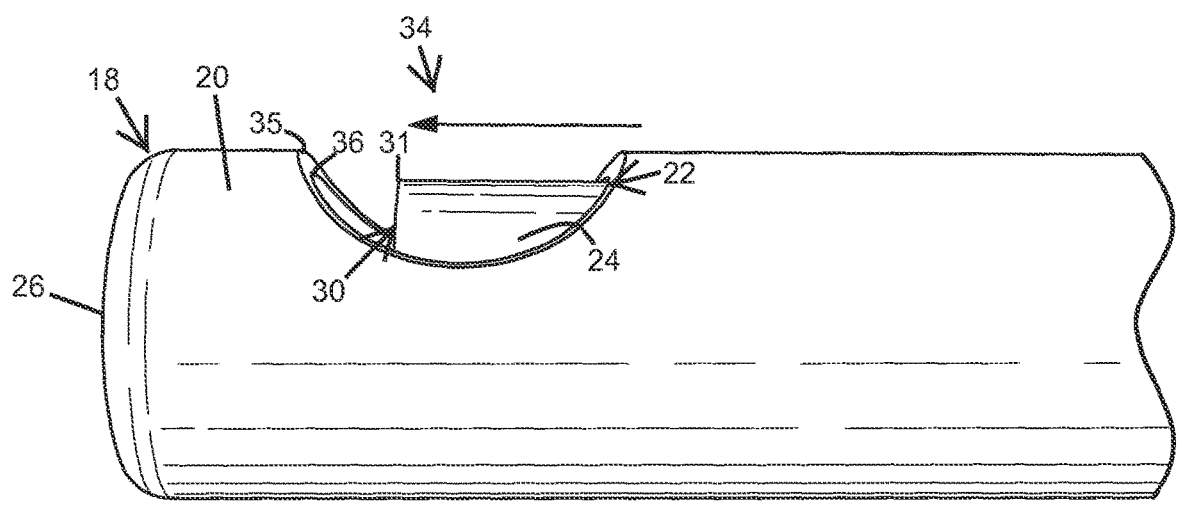
FIG. 5 is a side view of the aspirating cutter of FIG. 4 illustrating the inner tube moving relative to the outer tube.

In operation, aspiration (i.e., suction via negative pressure) is applied through the inner tube 22 and communicates through the open tip 30 to the port 34 in the outer tube 18, as indicated by arrows A in FIG. 4. The aspiration serves to draw vitreous material or other biological tissue into the port 34, where it can be cut. The cutting action is accomplished by sliding the inner tube 22 toward the closed tip 26 of the outer tube 18 such that the open tip 30 traverses the port 34 (FIG. 5). A scissors-like action occurs between the inner edge 36 of the port 34 and the outer edge 31 of the inner tube 22, slicing, cutting, or otherwise severing the biological material. After the material is cut, the aspiration (i.e., vacuum) serves to remove it through the inner tube 22.

FIGS. 6-10 illustrate a portion of an aspirating cutter 110 including an outer tube 118 and inner tubes 122a, 122b in accordance with other embodiment. Like features and components of the aspirating cutter 110 with respect to the aspirating cutter 10 are shown in the "100" series of reference numerals, the description of which need not be repeated. Like features and components of the inner tubes 122a, 122b shall additionally be indicated by adding "a" or "b" to the corresponding reference number of the inner tube 22.

Figure 6:
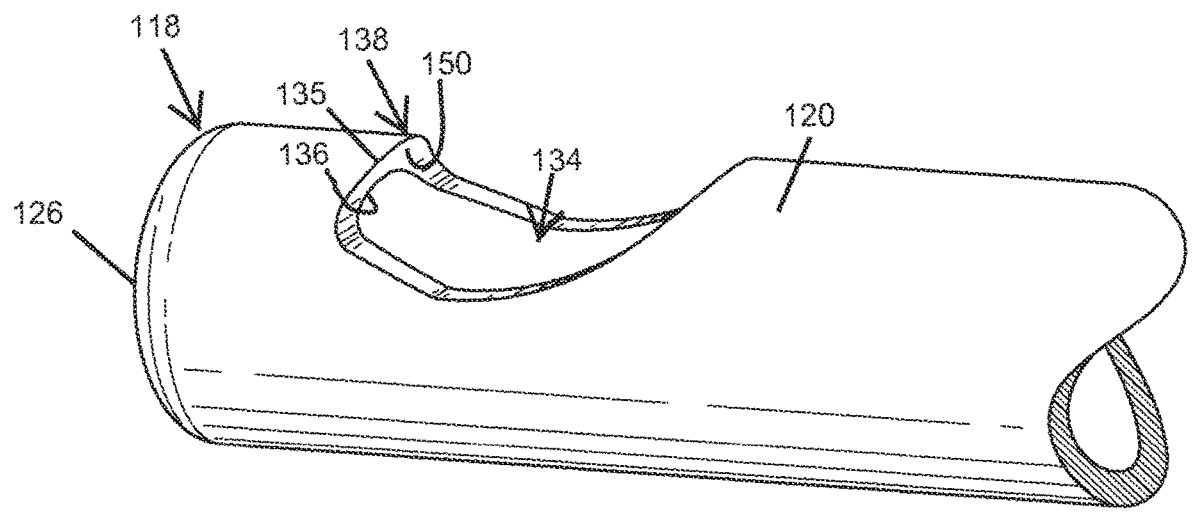
FIG. 6 is a perspective view of an outer tube of another aspirating cutter.

In the embodiment shown in FIG. 6, a port 134 of the outer tube 118 is partially defined by an angled feature in the form of an undercut lip 138 (i.e., a structure defining a space absent of material on an inner or lower part of the structure) itself formed as a portion of the annular side wall 120. The lip 138 is located on the side of the port 134 closest to the outer tube tip 126. The resulting inward-facing angled surface 150 is non-perpendicular to the longitudinal axis 123. Thus, the angled feature 138 presents an outer edge 135 of the port 134 that protrudes axially further from the tip 126 than the inner edge or cutting surface 136.

Figure 7:
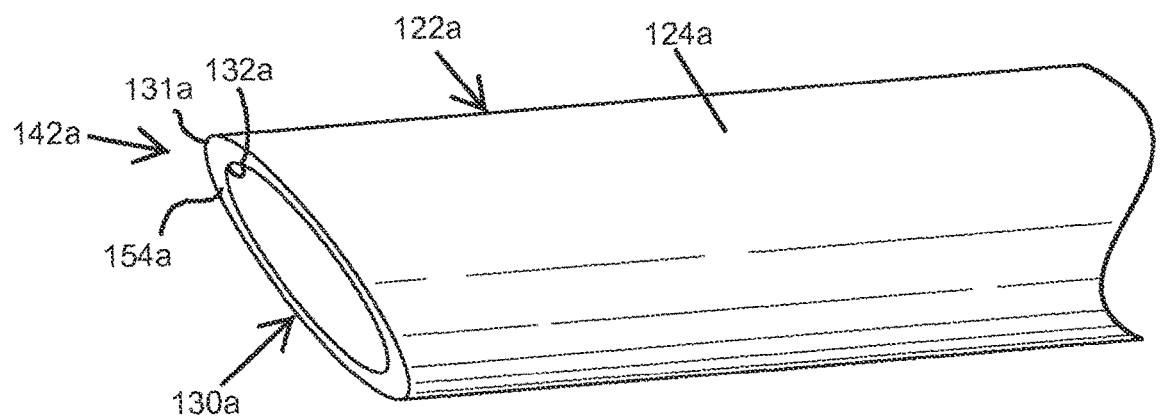
FIG. 7 is a perspective view of an inner tube of another aspirating cutter.

In reference to FIG. 7, the surface 154a of the open tip 130a of the inner tube 122a is non-perpendicular with the longitudinal axis 123 and presents an angled feature in the form of an undercut lip 142a itself formed as a portion of the annular side wall 124a. Thus, the angled feature 142a includes an outer edge or cutting surface 131a that extends further toward the closed tip 126 of the outer tube 118 (when assembled) than the inner edge 132a to.

Figure 8:
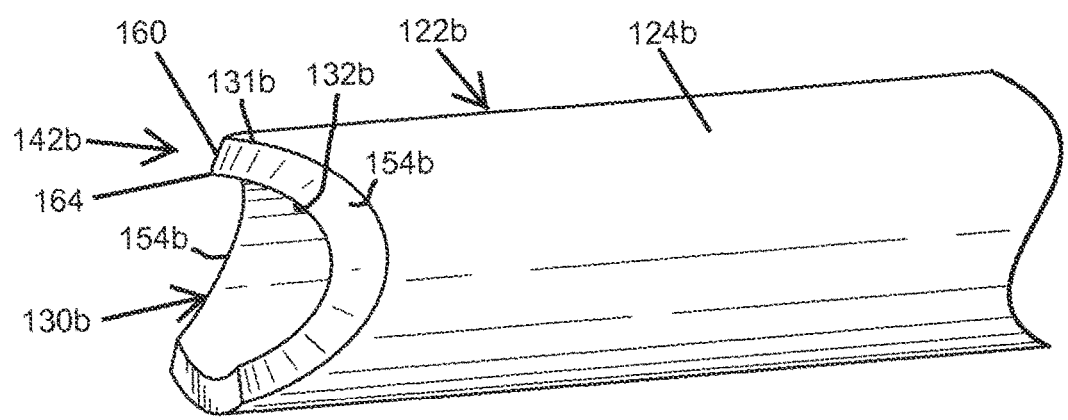
FIG. 8 is a perspective view of another inner tube of another aspirating cutter.

In reference to FIG. 8, a portion of the surface 154b of the open tip 130b is non-perpendicular with the longitudinal axis 123 and presents an angled feature in the form of a cusp 142b (i.e., a point formed by the intersection of two or more adjoining surfaces) itself formed as a portion of the annular side wall 124b. Specifically, the surface 154b defines an edge 160 having a point 164 that extends toward the closed tip 126 of the outer tube 118 (when assembled). More specifically, the edge 160 is formed by the intersection of two surfaces, i.e., opposing portions of the surface 154b at the open tip 130b. The edge 160 and outer edge 131b together form a cutting surface that does not extend as far toward the closed tip 126 as the inner edge 132b. In addition, the cusp 142b overhangs a diametrically opposed portion of the open tip 130b.

The complex geometry of the tubes 118, 122*a*, 122*b* may be fabricated using a wire electrical discharge machining ("EDM") process. Alternatively, or in addition, certain geometric features of the tubes 118, 122*a*, 122*b* may be formed by grinding and/or cutting the end of the tubes 118, 122*a*, 122*b* at the necessary angles.

Figure 9:
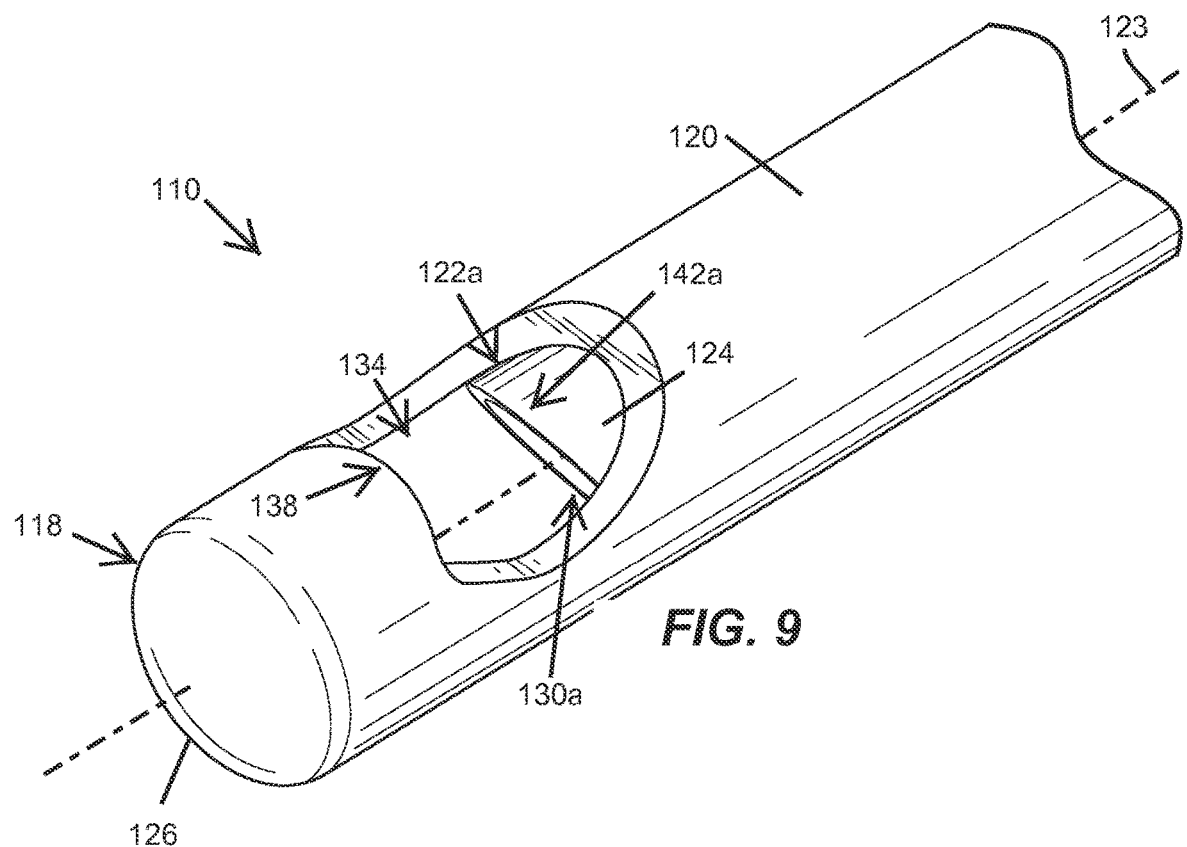
FIG. 9 is a perspective view of a portion of an aspirating cutter with the outer tube of FIG. 6 and the inner tube of FIG. 7.
Figure 10:
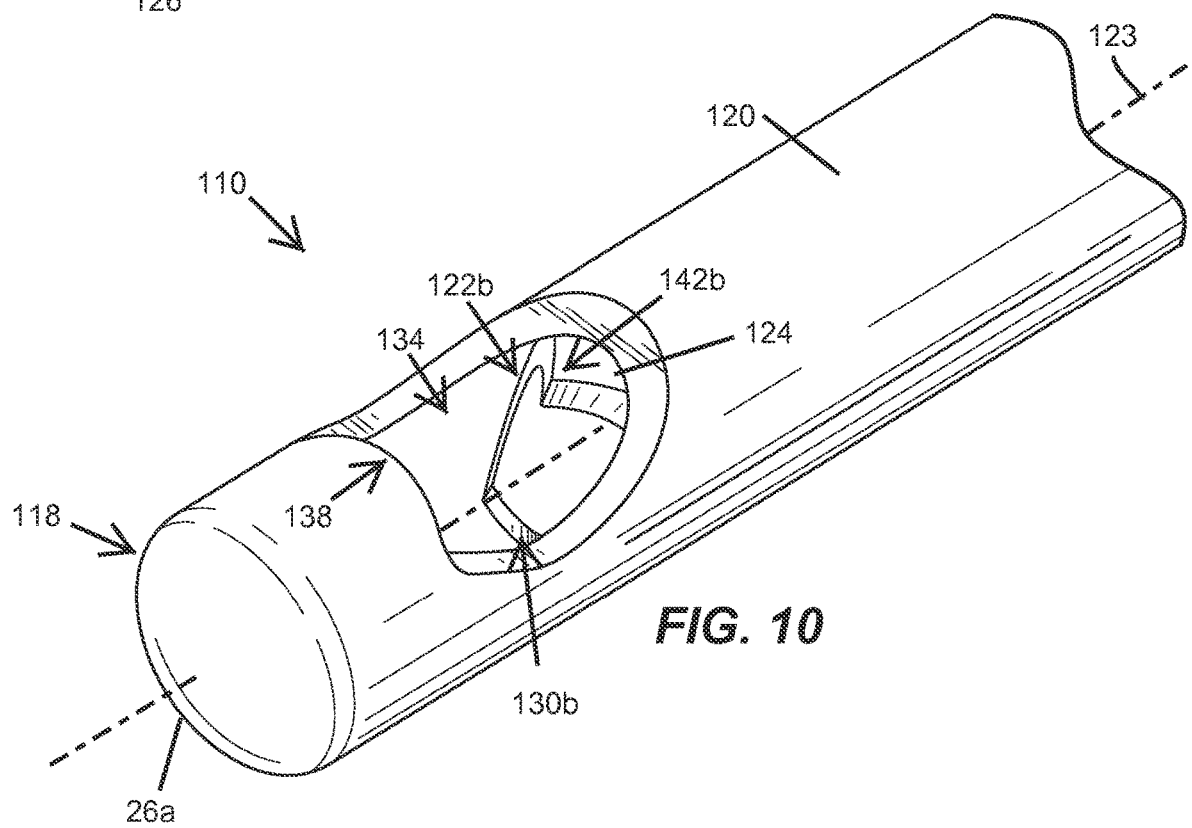
FIG. 10 is a perspective view of a portion of an aspirating cutter with the outer tube of FIG. 6 and the inner tube of FIG. 8.

Referring to FIGS. 9 and 10, in operation of the aspirating cutter 110, the inner tube 122*a*, 122*b* is actuated to move axially with respect to the outer tube 118 for cutting biological tissues in the port 134. The inner tube 122*a*, 122*b* is normally in the retracted position (FIGS. 9 and 10), leaving open the port 134 of the outer tube 118. Once biological material has entered the port 134, the inner tube 122*a*, 122*b* is actuated manually by the surgeon and/or automatically by a control system to advance to the extended position, similar to that shown in FIG. 5. During the extension of the inner tube 122*a*, 122*b*, material drawn into the port 134 and trapped between the undercut lip 138 and the surface 154*a*, 154*b* is directly radially inward by the inward-facing surface 150 and cut as the outer edge 131*a*, 131*b* of the open tip 130*a*, 130*b* is extended past the inner edge 136 of the port 134. The inner tube 122*a*, 122*b* is then returned to the retracted position. In some applications, the inner tube 122*a*, 122*b* may be actuated in a cyclical fashion at a predetermined operation frequency, as described in more detail below.

The geometric structures of the above-described angled features, i.e., the undercut lips 138, 142*a*, and the cusp 142*b*, increase the cutting performance of the inner tube 122*a*, 122*b* to initially crack or fragment hard cataract tissue. Specifically, the angled features interface during the cutting motion to create a stress concentration area for fracturing and cutting the hard biological tissue. With respect to inner tube 122*a*, the outer edge 13*a* of the open tip 130*a* provides a reduced contact area, thereby increasing contact pressure to assist in piercing hard biological tissues (e.g., cataracts). With respect to the inner tube 122*b*, the edge 160 and point 164 similarly provide a reduced area for the inner tube 122*b* to more effectively cut biological tissue. Moreover, as described above, the inward-facing surfaces 150, 154*a*, for example, help to hold biological tissue in place while the cutting force is applied by the transverse movement of the inner tube 122*a* relative to the outer tube 118, and generally direct the biological tissue radially inward into the port 134 of the outer tube 118 toward a common longitudinal axis 123 of the apparatus (FIGS. 9 and 10). This helps prevent the naturally tendency of the biological tissue to be pushed away by the application of force due to the generally convex shape of the lens.

Figure 11:
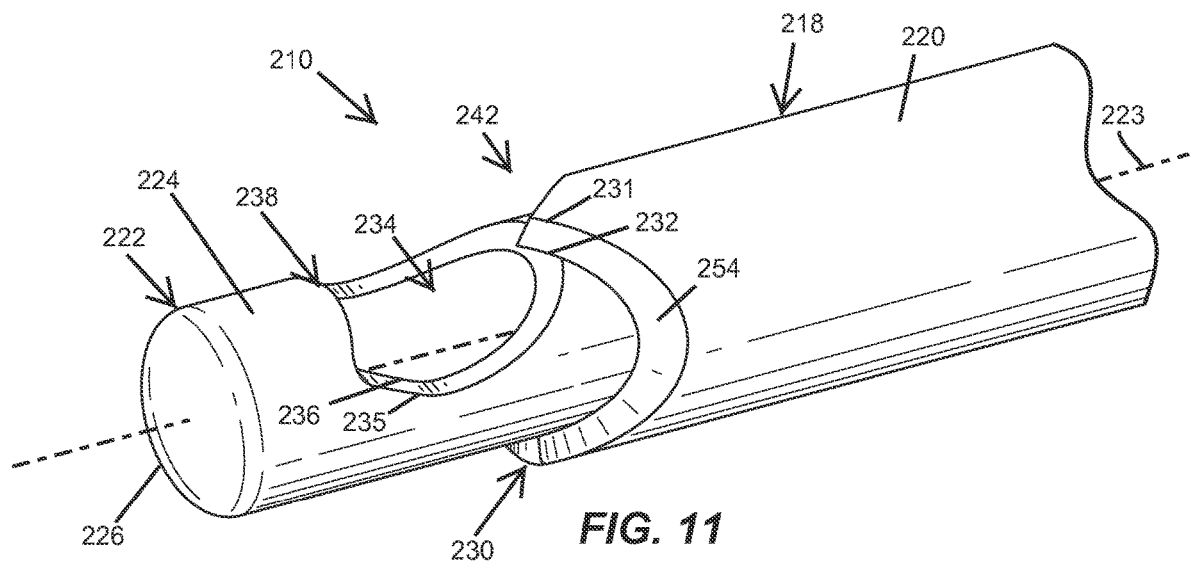
FIG. 11 is a perspective view of a portion of another aspirating cutter.
Figure 12:
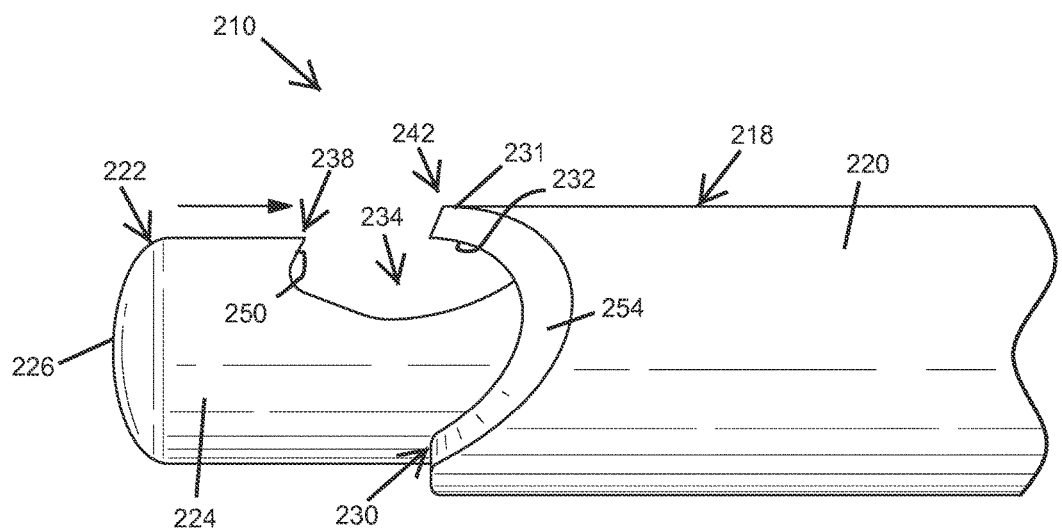
FIG. 12 is a side view of the aspirating cutter of FIG. 11 illustrating the inner tube moving relative to the outer tube.
Figure 13:
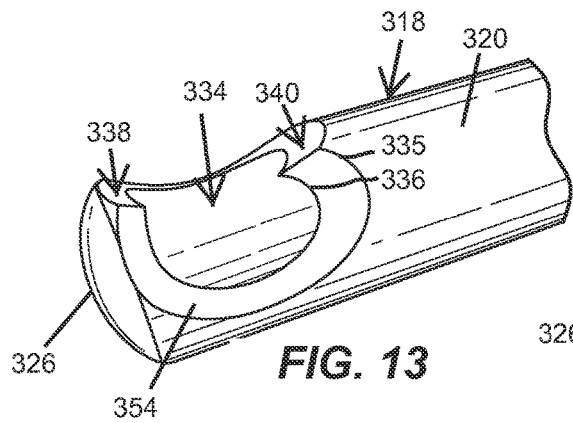
FIG. 13 is a perspective view of an outer tube of another aspirating cutter.
Figure 14:
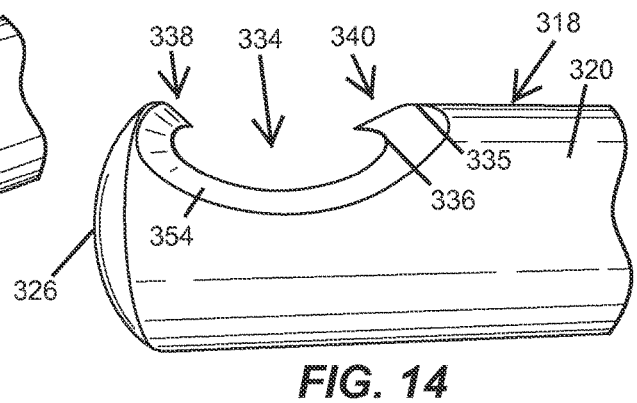
FIG. 14 is a side view of the outer tube of FIG. 13.
Figure 15:
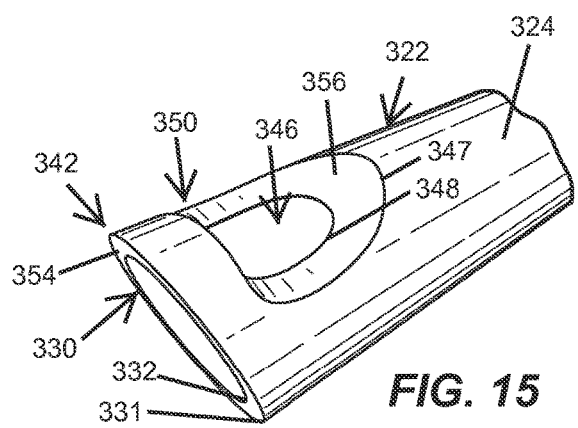
FIG. 15 is a perspective view of an inner tube of another aspirating cutter.
Figure 16:
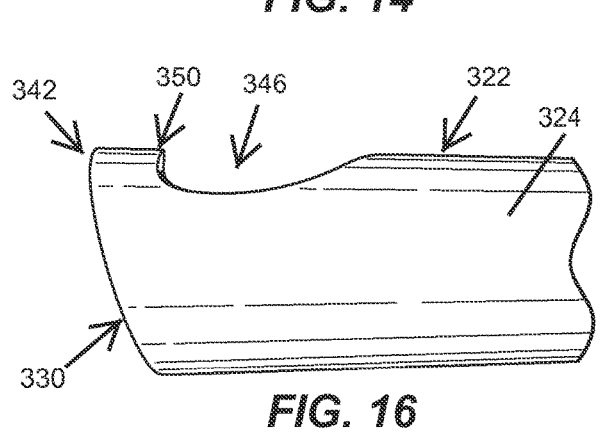
FIG. 16 is a side view of the inner tube of FIG. 15.

FIGS. 11 and 12 illustrate a portion of an aspirating cutter 210 in accordance with another embodiment having a reverse cutting construction. The aspirating cutter 210 includes an outer tube 218 and a coaxial inner tube 222 movable (i.e., slidable) relative to each other along a common longitudinal axis 223. While the orientation of the tubes 218, 222 are reversed, the structure of the outer tube 218 is similar to the construction of the inner tube 122*b* and the structure of the inner tube 222 is similar to the construction of the outer tube 118, the descriptions of which are equally applicable and hereby incorporated by reference. The sizes (e.g., diameters) of the tubes 118, 122*b* are switched to create the apparatus construction having tubes 218, 222. Like features and components of the aspirating cutter 210 to the aspirating cutter 110 are shown in the "200" series of reference numerals. The description of corresponding features and components are similar to the previously described features and components to which they correspond, and not hereby repeated.

The tubes 218, 222 include respective annular side walls 220, 224, constructed from, for example, surgical stainless steel. The tubes 218, 222 are configured in a reverse construction to that of aspirating cutter 110 (see FIGS. 6, 8, and 10). Specifically, the outer tube 218 includes an open tip 230, while the inner tube 222 includes a closed tip 226 at its end. The inner tube 222 includes an opening or port 234 for aspirating and/or cutting formed into the annular side wall 224 near the closed tip 226. The portion of the annular side wall 224 defining the rim of the port 234 includes an outer edge 235 and an inner edge 236, and the port 234 is partially defined by an angled feature in the form of an undercut lip 238. The open tip 230 of the outer tube 218 similarly includes an outer edge 231 and an inner edge 232, and presents an angled feature in the form of a cusp 242. The outer tube 218 is larger than the inner tube 222 such that the inner tube 222 is received inside the outer tube 218 and slidable within it. Further, the inner tube 222 is configured such that it extends beyond the open tip 230 of the outer tube 218.

In operation, aspiration (i.e., suction via negative pressure) is applied through the inner tube 222 and communicates through the port 234 in the inner tube 222. The aspiration serves to draw vitreous material or other biological tissue into the port 234, where it can be cut. The inner tube 222 is normally in the extended position (FIGS. 11 and 12), leaving open the port 234 of the inner tube 222. The inner tube 222 can be actuated manually or automatically to move to the retracted position, and then return to the extended position. During the retraction of the inner tube 222 further into the open tip 230 of the outer tube 218 such that the open tip 230 traverses the port 234 (FIG. 12), the material drawn into the port 234 is directly radially inward by the inward-facing surface 250 and cut as the inner edge 232 of the open tip 230 is extended past the outer edge 235 of the port 234, i.e., a scissors-like action occurs between the outer edge 235 of the port 234 and the inner edge 232 of the outer tube 218. After the biological material is cut, the aspiration serves to remove it through the inner tube 222.

Figure 19:
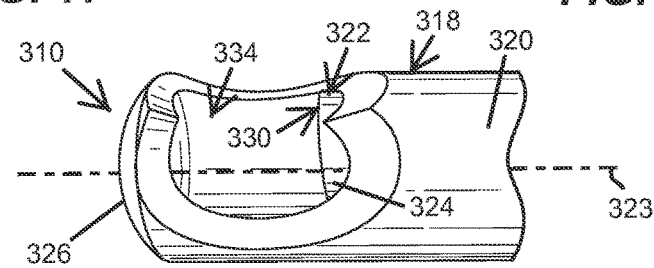
FIG. 19 is a perspective view of the aspirating cutter of FIG. 17, illustrating the inner tube in a retracted position.

FIGS. 13-19 illustrate portions of an aspirating cutter 310 with a construction wherein the cutter 310 is designed to cut both relatively soft and relatively hard tissue with or without an additional irrigation and aspiration ("I/A") instrument, as is described in greater detail below. In the illustrated embodiment, the aspirating cutter 310 includes an outer tube 318 and a coaxial inner tube 322 movable (i.e., slidable) relative to each other along a common longitudinal axis 323 (FIG. 19). The tubes 318, 322 include respective annular side walls 320, 324, constructed of, for example, surgical stainless steel.

The outer tube 318 includes a closed tip 326 and a first port 334 formed in the annular side wall 320 near the closed tip 326 for aspirating and/or cutting. The portion of the annular side wall 320 defining the rim of the first port 334 includes an outer edge 335 and an inner edge 336 and a face 356 therebetween. The first port 334 includes a first angled feature or cusp 338 near the closed tip 326 and a second angled feature or cusp 340 further from the closed tip 326. The cusps 338, 340 are similar in structure to cusps 142*b*, 242 described above.

The inner tube 322 includes an open tip 330 at its end and a port 346 formed in the annular side wall 324. The portion of the annular side wall 324 defining the rim of the port 346 includes an outer edge 347 and an inner edge 348, and the second port 346 also has an angled feature or undercut lip 350 near the open tip 330. The open tip 330 of the inner tube 322 includes an outer edge 331 and an inner edge 332 and is formed similarly to the open tip 130a of the inner tube 122a (FIG. 7), i.e., the open tip 330 includes an angled feature or undercut lip 342 similar in structure to the undercut lip 142a. The outer tube 318 is larger than the inner tube 322 such that the inner tube 322 is received inside the outer tube 318 and slidable within of it.

In general operation, aspiration (i.e., suction via negative pressure) is applied through the inner tube 322 and communicates through one or both of the first and second ports 334, 346, depending on the position of the tubes 318, 322 with respect to each other and the operational mode of the cutter 310. The aspiration serves to draw vitreous material or other biological tissue into the ports 334, 346. Cutting action is accomplished by sliding the inner tube 322 with respect to the outer tube 318, so that the open tip 330 traverses the first port 334 and/or the cusp 340 of the first port 334 traverses the second port 346. In particular, the undercut lip 342 of the open tip 330 at the outer edge 331 and the cusp 338 of the first port 334 at the inner edge 336 interface during a cutting motion to create a first stress concentration area for fracturing and cutting biological materials and directing the cut materials radially inward into the first port 334. The undercut lip 350 of the second port 346 at an outer edge 347 interfaces with the cusp 340 of the first port 334 at the inner edge 336 to create a second stress concentration area, similar to the first stress concentration area and in a similar manner as described with respect to FIGS. 11 and 12. In both cases, a scissors-like action occurs between the cusps 338, 340 and the corresponding undercut lips 342, 350. After the biological material is cut, the aspiration serves to remove it through the inner tube 322. The aspirating cutter 310 may be operated in several different modes.

Figure 17:
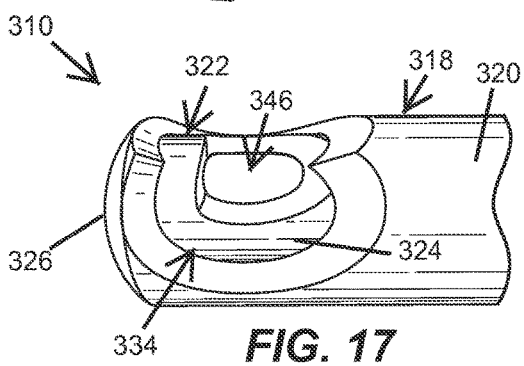
FIG. 17 is a perspective view of a portion of an aspirating cutter with the outer tube of FIG. 13 and the inner tube of FIG. 15, illustrating the inner tube in an extended position.
Figure 18:
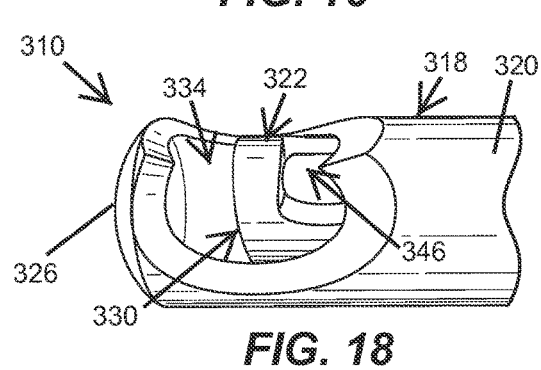
FIG. 18 is a perspective view of the aspirating cutter of FIG. 17, illustrating the inner tube in an intermediate position.
Figure 20:
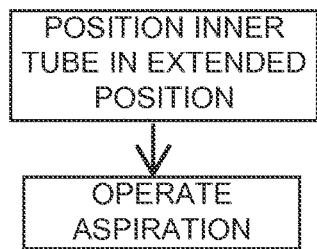
FIG. 20 is a flow chart of a first method of operating an aspirating cutter.

In a first mode of operation (FIG. 20), the inner tube 322 is kept extended (FIG. 17). In this configuration, although the port 334 of the outer tube 318 is partially obstructed by the inner tube 322, the port 346 of the inner tube 322 is aligned with the port 334, providing a path for aspiration through both the port 334 and the second port 346. In this mode of operation, the instrument can be used similar to a conventional I/A instrument, in which the level of vacuum is continually increased to attract, hold, and extrude cortical material through the ports 334, 346 without any additional mechanical motion (e.g., cutting, etc.).

Figure 21:
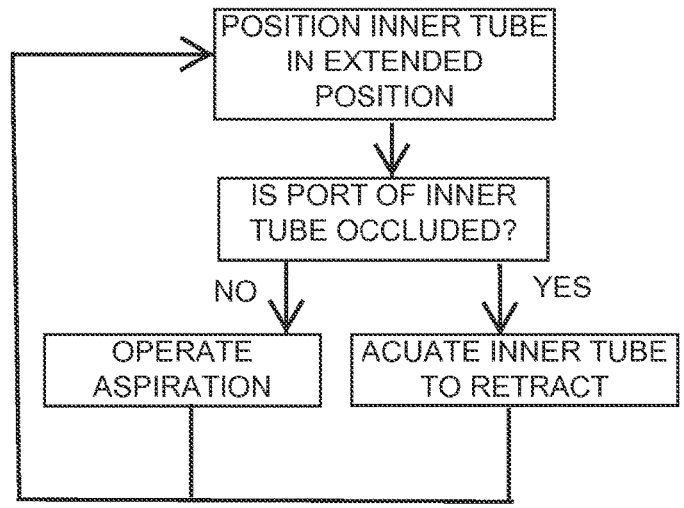
FIG. 21 is a flow chart of a second method of operating an aspirating cutter.

In a second mode of operation (FIG. 21), the inner tube 322 is initially positioned in the extended position. The inner tube 322 can be operated, however, to briefly move from the extended position to a retracted position (FIG. 19), thereby cutting material held within the port 346 and/or drawing material into the port 334 as it opens. Upon returning the inner tube 322 to the extended position (FIG. 17), any material held within the port 334 is cut, as previously described.

As an example, the aspirating cutter 310 may be operated as a conventional I/A instrument until material is encountered which is unable to be extruded through the ports 334, 346. The inner tube 322 of the aspirating cutter 310 may then be actuated by the surgeon and moved relative to the outer tube 318, breaking the suction connection and cutting occluding material. Because the aspiration inside inner tube 322 builds to a high level while the smaller port 346 is occluded, there is a surge in suction which occurs when the larger port 334 is opened by the withdrawal of the inner tube 322. This surge helps to draw at least a portion of the occluding material into the larger port 334 of the outer tube 318. An operating cycle can be timed so that the inner tube 322 re-extends while the surge is at its peak, maximizing the amount of material which is captured and cut. After the section of occluding material is removed from the operational site, the surgeon may then resume operation of the aspirating cutter 310 as an I/A instrument. While in the second mode of operation, the scissors-like motion of the inner tube 322 relative to the outer tube 318 may be automatically actuated via a control system that senses the pressure within aspirating cutter 310 and/or actuated manually via an actuator (not shown) engageable by the surgeon, such as a foot pedal.

Figure 22:
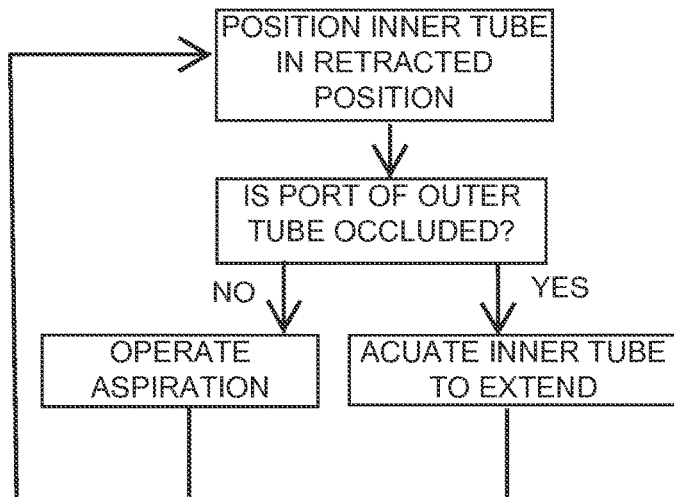
FIG. 22 is a flow chart of a third method of operating an aspirating cutter.

In a third mode of operation (FIG. 22), the cutting cycle of the second mode is reversed. The inner tube 322 is initially positioned in the retracted position (FIG. 19), leaving open the larger port 334 of the outer tube 318. The inner tube 322 can be actuated to briefly move to the extended position (FIG. 17). Material drawn into the port 334 is therefore cut as the open tip 330 of the inner tube 322 is extended past the edge 336 of the first port 334 near the closed tip 326. As the inner tube 322 slides back toward the retracted position, material held within the port 346 may be further cut.

In any of these operating modes, the cutting action of the aspirating cutter 310 may be enhanced by one of the features designed to increase stress or cutting pressure, as described above with respect to the aspirating cutters 10, 110, 210. The aspirating cutter 310 illustrated in FIGS. 13-19 includes cusp features 338, 340 at both ends of the port 334 in the outer tube 318, an undercut lip 342 at the open tip 330 of the inner tube 322, and an undercut lip 350 on the port 346 of the inner tube 322.

The arrangement of stress increasing features (e.g., undercut lips, cusps, etc.) for the aspirating cutters 10, 110, 210, 310 may be altered in alternative embodiments. For example, angled features may be presented on either the upper or lower edges of the annular side walls that form the cutting features (e.g., open tip, cutting ports, etc.). The angled features may be presented on portions near or distant to the open or closed-tips of the tubes. Additionally, any number of angled features may be used, e.g., a particular cutter may include a plurality of ports, each including a combination of one or more angled features.

The aspirating cutters 10, 110, 210, 310 may be pneumatically-operated. Specifically, the movement of the inner tube 22, 122a, 122b, 222, 322 in relation to the outer tube 18, 118, 218, 318, which performs the cutting action of the device, is pneumatically driven at high rates to perform such cutting operations. In some applications, the aspirating cutter handpiece receives pneumatic power from a vitreoretinal surgical system or console (not shown), which may also provide aspiration and illumination functions. The pneumatic aspirating cutter may cut at a rate up to 8,000 cuts per minutes ("CPM") for vitreous cutting applications. For cataract cutting applications, more time is needed per cut to move the dense material of the cataract into the port. As an example, a useful cut rate may be around 300 CPM for cataract cutting applications. However, the aspirating cutters 10, 110, 210, 310 may also be configured to cut at rates lower or higher than 300 CPM while cutting cataract biological tissue. The surgical system produces pulse trains related to a user-selected operating frequency.

The handpiece (i.e., handle 12) of the pneumatically-operated aspirating cutter includes a flexible diaphragm or piston biased in a first direction via a biasing element or spring. When the aspirating cutter is in use, an actuating pulse is delivered through a set of actuation tubing in fluid communication with the diaphragm or piston to overcome the biasing force of the spring and move the diaphragm or piston in a second direction. Movement of the diaphragm or piston in the second direction causes the inner tube to move across the port defined by the outer tube and cut material that is located within the port. Therefore, an actuation pulse train will cause the inner tube to move in the first and second directions in a cyclic fashion. Additionally, negative pressure is conducted through a set of aspiration tubing fluidly connected to the aspiration port to aspirate cut tissues from the surgical site.

Depending on the hardness of the cataract, the aspirating cutters 10, 110, 210, 310 described above may or may not be capable of making the initial cut in a shell of extremely hardened material. The onion-layer structure of the lens makes it much easier to peel and dissect layers once a break has been created and an edge exposed. Accordingly, the scope of this invention includes a method of use in which one or more additional instruments are used to precondition the lens for easier removal with the aspirating cutter.

Figure 23:
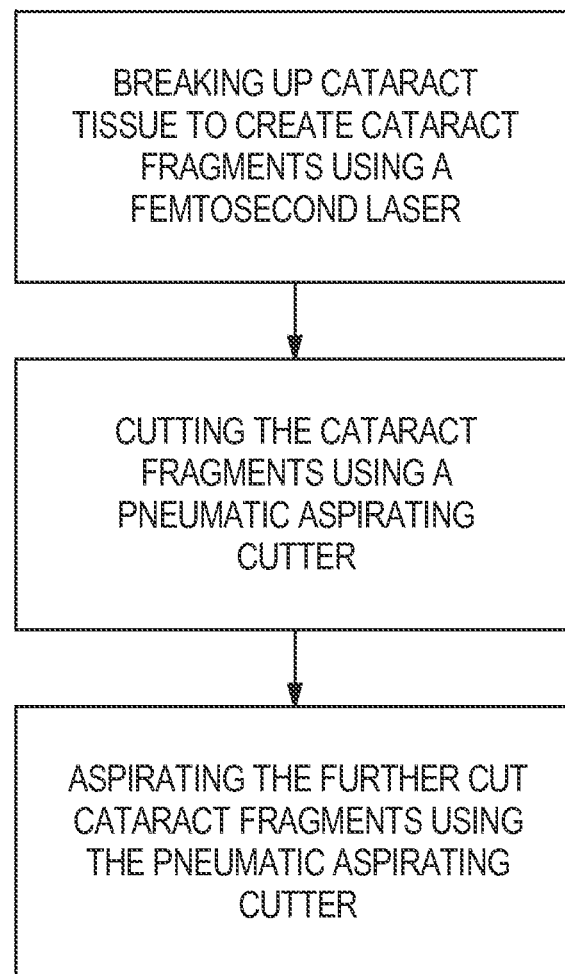
FIG. 23 is a flow chart of a method of using an aspirating cutter in combination with a femtosecond laser.

In particular, the aspirating cutters 10, 110, 210, 310 described above may be used in combination with a femtosecond laser surgical procedure, as illustrated in FIG. 23. This procedure involves the transmission of laser pulses toward a portion of cataract tissues within a patient's eye. The laser pulses break apart or fragment the hardened cataract tissue to create cataract fragments smaller than the original cataract tissue mass. Once the cataract tissue is fragmented, the aspirating cutter would be used, as described above, to further cut the cataract fragments into smaller pieces. The smaller pieces are then aspirated through the port of the outer tube and removed from the surgical site. Due to the reduced size of the smaller pieces, the efficiency of aspiration is increased. In an alternative embodiment, the laser may be any other type of laser or optical device sufficient to fragment or cut the original cataract tissue mass or any other desired tissues.

The aspirating cutters described above may also be used in combination with instruments that mechanically fracture the lens. Several such instruments, including the "lens chopper," are known in the art. Hardened layers of the lens are also brittle, and tend to fracture along radial planes of cleave naturally present in the lens structure. Once fractured in this manner, the edges of the layers are exposed and easily engaged by the aspirating cutter.

Various features and advantages of the invention are set forth in the following claims.

What is claimed is:

1. A surgical cutting apparatus for cutting biological material, the apparatus comprising:
   a handle;
   an outer tube attached to the handle and having a closed tip, wherein the outer tube extends along a longitudinal axis;
   a port formed in a side wall of the outer tube; and
   an inner tube slidable within the outer tube along the longitudinal axis and having an open tip, the inner tube being in fluid communication with the handle,
   wherein the outer tube includes a cusp, wherein the cusp is defined by an intersection of a first surface and a second surface, wherein the first surface and the second surface extend around the port in the side wall of the outer tube, wherein the first surface and the second surface intersect at an edge, and wherein the edge extends at an oblique angle relative to the longitudinal axis.

2. The surgical cutting apparatus of claim 1, wherein the surgical cutting apparatus is pneumatically-powered.

3. The surgical cutting apparatus of claim 1, wherein the open tip of the inner tube is formed with an angled feature, and wherein the angled feature of the inner tube is formed by an angled surface, the angled surface being non-perpendicular with the longitudinal axis of the inner tube.

4. The surgical cutting apparatus of claim 3, wherein the angled feature of the inner tube is an undercut lip.

5. The surgical cutting apparatus of claim 1, wherein the cusp is a first cusp, the intersection is a first intersection, and the edge is a first edge, wherein the outer tube includes a second cusp located opposite the first cusp, wherein the second cusp is defined by a second intersection of the first surface and the second surface, wherein the second intersection defines a second edge, wherein the second edge extends at an oblique angle relative to the longitudinal axis.

6. The surgical cutting apparatus of claim 5, wherein the first edge extends along a first axis and the second edge extends along a second axis, wherein the first axis intersects the second axis.

7. A surgical cutting apparatus for cutting biological material, the apparatus comprising:
   a handle;
   an outer tube attached to the handle and having a closed tip, wherein the outer tube extends along a longitudinal axis;
   a first port formed in a side wall of the outer tube, the first port including a first cusp and a second cusp located opposite the first cusp, wherein the first and second cusps are the only cusps of the first port, wherein a first, curved surface extends between the first cusp and the second cusp and defines a first curved edge of the first port, and wherein a second, curved surface extends between the first cusp and the second cusp and defines a second curved edge of the first port, wherein the first cusp is defined by a first intersection of the first surface and the second surface, and wherein the second cusp is defined by a second intersection of the first surface and the second surface;
   an inner tube slidable within the outer tube and having an open tip, the inner tube being in fluid communication with the handle; and
   a second port formed in a side wall of the inner tube,
   wherein the cusp of the first port and the open tip of the inner tube interface during a cutting motion to fracture and cut biological materials and direct cut materials radially inward into the first port, and
   wherein the first and second ports overlap when the inner tube is in an extended position within the outer tube.

8. The surgical cutting apparatus of claim 7, wherein the surgical cutting apparatus is pneumatically-powered.

9. The surgical cutting apparatus of claim 7, wherein the first surface and the second surface each extend at an oblique angle relative to the longitudinal axis.

10. The surgical cutting apparatus of claim 7, wherein the first intersection defines a first edge and the second intersection defines a second edge, wherein both the first edge and the second edge extend at an oblique angle relative to the longitudinal axis.

11. The surgical cutting apparatus of claim 10, wherein the first edge extends along a first axis and the second edge extends along a second axis, wherein the first axis intersects the second axis.

* * * * *